(12) United States Patent
D'Antonio (10) Patent No.: US 6,955,664 B2
(45) Date of Patent: Oct. 18, 2005

(54) SUCTION REGULATOR AND FLUID DRAINAGE SYSTEM

(75) Inventor: Nicholas F. D'Antonio, Tully, NY (US)

(73) Assignee: D'Antonio Consultants International, Inc., E. Syracuse, NY (US)

( * ) Notice: Subject to any disclaimer, the term of this patent is extended or adjusted under 35 U.S.C. 154(b) by 89 days.

(21) Appl. No.: 10/196,706

(22) Filed: Jul. 15, 2002

(65) Prior Publication Data

US 2003/0028175 A1 Feb. 6, 2003

Related U.S. Application Data

(60) Provisional application No. 60/306,024, filed on Jul. 17, 2001.

(51) Int. Cl.[7] .......................... A61M 1/00; F16K 31/12; F16K 15/00
(52) U.S. Cl. ...................... 604/323; 604/118; 604/315; 604/319; 137/505; 137/526; 251/205
(58) Field of Search .................... 604/118–121, 315, 604/317–327; 137/505.11, 505, 511, 526; 138/45, 46, 78.5; 600/573, 579; 601/6–14; 251/205, 208

(56) References Cited

U.S. PATENT DOCUMENTS

| | | | | |
|---|---|---|---|---|
| 3,763,884 A | * | 10/1973 | Grassi et al. | 137/504 |
| 3,830,238 A | * | 8/1974 | Kurtz et al. | 604/318 |
| 3,863,671 A | * | 2/1975 | Heimann | 137/526 |
| 4,109,683 A | * | 8/1978 | Strache | 137/625.3 |
| 4,468,226 A | * | 8/1984 | Kurtz et al. | 604/321 |
| 4,698,060 A | * | 10/1987 | D'Antonio et al. | 604/320 |
| 4,715,855 A | * | 12/1987 | D'Antonio et al. | 604/320 |
| 4,889,531 A | * | 12/1989 | D'Antonio et al. | 604/319 |
| 4,902,284 A | * | 2/1990 | D'Antonio et al. | 604/320 |
| 5,256,160 A | * | 10/1993 | Clement | 604/319 |
| 5,269,768 A | * | 12/1993 | Cheung | 604/248 |
| 5,423,780 A | * | 6/1995 | Malette | 604/317 |
| 5,458,138 A | * | 10/1995 | Gajo | 128/205.24 |
| 5,507,734 A | * | 4/1996 | Everett et al. | 604/320 |
| 5,707,356 A | * | 1/1998 | Paul | 604/119 |
| 5,730,727 A | * | 3/1998 | Russo | 604/118 |
| 6,024,120 A | * | 2/2000 | Yam et al. | 137/495 |
| 6,338,728 B1 | * | 1/2002 | Valerio et al. | 604/317 |
| 6,368,310 B1 | * | 4/2002 | Bemis et al. | 604/319 |
| 6,468,229 B1 | * | 10/2002 | Grace et al. | 600/573 |

(Continued)

Primary Examiner—Larry I. Schwartz
Assistant Examiner—Michael G. Bogart
(74) Attorney, Agent, or Firm—D. Peter Hochberg; Sean Mellino; Katherine R. Vieyra (57) ABSTRACT

A low cost suction regulator is disclosed in conjunction with a fluid drainage system that includes a suction chamber and a collection chamber. The suction regulator is comprised of an atmospheric chamber and a suction chamber separated by a divider. An opening in the divider has a variably biased closing member associated therewith for opening or closing the opening according to operator selected pressure differentials between the chambers. The closing member is movable along an axis that differs from the direction of airflow, thus eliminating the need for damping the forces applied to the closing member. The dividing means and its closing member will operate over the full range of angles from the vertical to horizontal axis. One embodiment of the drainage system further includes devices for measuring patient airflow, patient negativity and imposed suction. Measurement of these variables is effectively implemented with diaphragms or bellows having dials or other types of marker connected thereto such that movement of the diaphragm or bellows results in movement of the dial or marker to thereby indicate the value of the above noted variables.

35 Claims, 7 Drawing Sheets

U.S. PATENT DOCUMENTS 6,514,232 B1 * 2/2003 Gibertoni ..................... 604/247
6,585,708 B1 * 7/2003 Maaskamp .................. 604/317
6,673,055 B2 * 1/2004 Bemis et al. ................ 604/319
6,749,592 B2 * 6/2004 Lord .......................... 604/319
2004/0102743 A1 * 5/2004 Walker ....................... 604/319

* cited by examiner

SUCTION REGULATOR AND FLUID DRAINAGE SYSTEM

CROSS REFERENCE TO RELATED APPLICATION

This application claims priority of U.S. Provisional Application No. 60/306,024, filed Jul. 17, 2001, under Title 35, United States Code, Section 119(e).

BACKGROUND OF THE INVENTION

1. Field of the Invention

This invention relates to fluid pressure regulating systems, such as systems for regulating the pressure of gas. The invention further relates to controlling the pressure of suction flow lines and suction chambers, and in particular as applied to wound drainage systems, for draining fluids from medical patients, such as from the chest cavity, by means of gas pressure differentials using low pressure gas systems.

2. Description of the Prior Art

In many situations involving gases, it is important, and often mandatory, to measure and regulate the pressure of the gas. In one important example, there exists in hospitals a system for distributing vacuum or suction from a central vacuum supply system, which in many cases must be monitored and regulated when it is used. These systems are used, for example, in conjunction with wound drainage devices, where fluids, such as blood and water, and gas from a wound in a patient's pleural cavity are withdrawn using a pressure differential established between a controlled suction chamber and the internal pressure in the patient. Such suction pressure and pressure differentials must be closely controlled because of the dangerous conditions which could result if unduly high or low pressure differentials should occur. In this application, as in many other pressure measuring and regulating applications, it is desirable to incorporate a pressure regulating device which is compact, which makes the pressure measurement and regulation with accuracy, which is capable of functioning reliably for long periods of time, and which is economical to manufacture.

A particularly advantageous system is disclosed in U.S. Pat. Nos. 4,698,060, 4,715,855 and 4,889,531, which are incorporated herein by reference, as well as PCT publication number WO 00/78373 A2, each of which discloses a pressure regulator and a fluid drainage system. The pressure regulator includes high and low pressure chambers separated by a divider having an opening, a closing member biased to a closing position for closing the opening with a biasing force according to a desired pressure differential between the chambers, and a damping device for damping the resulting force, and movement, on the closing member. The fluid drainage system has a suction chamber with a suction regulator and various arrangements of diaphragms for measuring pressure differentials. As economical as these systems are, they do incorporate the relatively expensive damping device, such as a dashpot, for effectively damping the force applied by the closing member in order to prevent undesirable vibration at the transition point.

U.S. Pat. No. 3,830,238, illustrates movement of a bellows assembly to detect and display the value of negativity within the pleural cavity while U.S. Pat. No. 4,468,226 discloses a bellows device which contracts as suction increases in a collection chamber. An indicator vane, connected to the bellows, moves along a fixed scale to indicate the level of suction within the collection chamber. While both of these disclosures are directed to chest drainage devices, neither of them is used to control the level of suction or negativity in the system.

SUMMARY OF THE INVENTION

It is an object of the invention to provide an improved device for regulating the pressure of a gas in one space relative to the pressure of a gas in another space which is in communication with the first space.

Another objective is to accurately regulate a selectively variable pressure to a suction chamber relative to the atmosphere by means of an economical yet effective device.

A further object of the present invention is to provide an improved gas pressure regulating device including an opening through which high pressure air can flow from a first space to a second space having a lower pressure, and a means for selectively closing the opening in a smooth manner without the use of a damper for controlling the effect of force, and the tendency of surface contact vibration, on the device for closing the opening.

It is still another object of the present invention to provide an improved chest drainage system for regulating the suction pressure in an accurate and efficient way using economical components.

Yet another important objective of the present invention is to provide a suction chamber that will preferentially draw air from a patient air leak in the chest cavity before drawing additional air from the atmosphere in order to satisfy the total volume of air needed to maintain the selected value of pressure in the suction chamber.

Still yet another object of the present invention is to provide an improved gas pressure regulating device and chest drainage system in a more economical manner.

These and other objects will occur to those skilled in the art from the description to follow.

The foregoing objects are achieved according to a preferred embodiment of the invention by means of a system having a first chamber or atmospheric chamber with access to the atmosphere and a second chamber or suction chamber in communication with a suction line, the system having two active members. The first chamber is under atmospheric pressure and the second chamber communicates with the airflow and pressure associated with a patient. The device controls access of the second chamber to the atmosphere to thereby regulate the pressure in the second chamber which is communicating with the suction line. The first of the active members for controlling access to the atmosphere is a movable member or closure, preferably a sliding door structure, which is captured by a capturing, guiding or holding device such as rails or brackets, and is movable to open or close an air or other gas path between the second chamber and the first chamber ("the thru-put path"). Movement of the sliding door is provoked with the deflection of the second of the active members which is a pressure sensitive device or pressure sensor, such as a pressure sensitive diaphragm, bellows, balloon, or the like. The sliding door is preferably very light in weight in order to reduce its drag while moving under the influence of changes in suction. The diaphragm is under the influence of a biasing force, and can be biased by means of a spring, which can be either a tension spring or a compression spring, whose setting is preferably adjusted by a pressure regulating apparatus according to the desired pressure applied to the patient. The pressure regulating apparatus advantageously has a setting member, such as a threaded shaft, for cooperating with the pressure sensitive device (or pressure sensor) for controlling the biasing force, and for assisting in indicating the desired suction pressure as well as the actual suction pressure. The sliding door, or other movable member used for sealing or otherwise controlling the opening, is advantageously mounted for low friction movement in response to diaphragm, bellows, balloon or other movement under the influence of the pressure differential between the first and second chambers. While the preferred embodiments illustrate the axis for door movement being perpendicular to the axis of atmospheric airflow through the divider, any angle will be free of surface contact vibration so long as the opening at the transition point is a captured sliding movement as opposed to the method for opening and closing the thru-put path disclosed in the prior art. Finally, the description of the invention has been described with the closing member being movable in an axis parallel with the dividing member; however, the control surfaces need not be flat, but could also be non-flat surfaces such as cylindrical or spherical members that rotate with respect to each other to open and close the thru-put path.

BRIEF DESCRIPTION OF THE DRAWINGS

FIG. 5 is an end view cross section somewhere along the opening for admitting atmospheric air in the embodiments of FIGS. 2 thru 4 and illustrates three possible structures for capturing the sliding door in order to prevent its movement away from the dividing member, shown as FIGS. 5A, 5B and 5C.

DETAILED DESCRIPTION OF THE PREFERRED EMBODIMENTS

Figure 1:
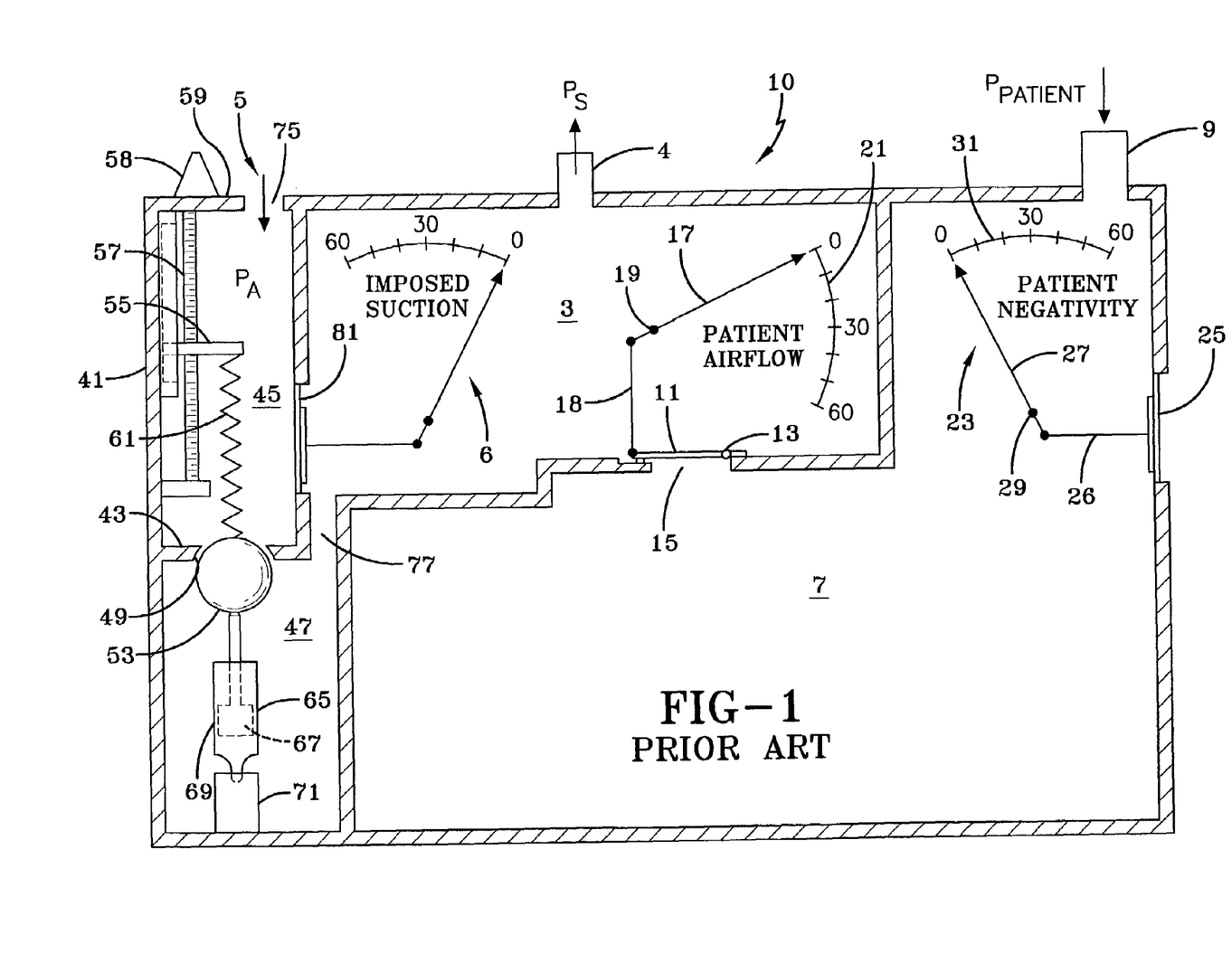
FIG. 1 is a schematic front view of the suction regulator according to the prior art system included herein by reference.

The figures and description to follow are primarily intended to illustrate the concept for a new, simplified, and more economical suction regulator, and in particular, for its use as a source of dry suction in a chest drainage device. FIG. 1 is a drawing taken from the prior art patents discussed above and included herein for reference, and provides a view of the earlier dry regulator for easy comparison to the present disclosure herein. It is noted that FIG. 1, and all the figures to follow, show a single chamber for the collection of fluids; however, the collection chamber is typically divided into smaller sections for better resolution when reading the value of fluid collected, wherein each of the collection chamber sections can be provided with anti-spill over capability between compartments as the volume collected increases. One such anti-spill over device is that disclosed in U.S. Pat. No. 4,902,284, included herein by reference. Further, the drawings are not shown in the correct perspective so far as the calibrated scale and pointer movement are concerned, for example, threaded rod 157 (discussed in detail below) in FIG. 2 has a very narrow waist 101 at the point where a tension spring 102 is connected so that rotation of adjustment knob 158 will only increase spring tension by a small amount, while at the same time, moving pointer 108 a large distance on a wider diameter portion of shaft or rod 157 as pointer 108 traverses calibrated scale 110, therein providing a display for the selected value of suction. That is, large movements on pointer 108 will only cause small movement on a tension spring 102. In addition, these figures do not include a detailed description of the usual components for patient air leak, patient negativity, anti-spill device and protection against reverse pressure to the patient; these components could advantageously be included in the system and are shown, for example, in U.S. Pat. Nos. 4,698,060, 4,715,855 and 4,889,531, which, as indicated above, are incorporated herein by reference.

Referring to FIG. 1, a wound drainage system 10 according to the prior art is disclosed comprising a suction compartment or chamber 3 from which air can be evacuated by an external vacuum source such as a centrally located vacuum pump in a hospital, a suction port 4 for interconnecting chamber 3 with the external vacuum source, a suction regulator 5 for controlling the pressure in chamber 3, a suction measuring device 6, a collection chamber 7 for collecting fluids withdrawn from a patient, and an inlet port 9 for connecting compartment or chamber 7 to the patient. A one-way patient airflow flap valve 11 mounted on a hinge 13 separates suction chamber 3 and collection chamber 7. Air evacuated from a patient through inlet port 9 passes through port 15 whenever the pressure in chamber 7 exceeds that in chamber 3, and the extent of that airflow is reflected by the amount flap valve 11 opens. Valve 11 is configured to close and seal port 15 when the pressure in suction chamber 3 exceeds that in collection chamber 7. A dial 17 mounted on a pivot 19 and movable by a push rod 18 attached to flap valve 11 cooperates with a calibrated scale 21 to indicate the patient airflow rate (generally in liters per minute) through port 15 according to the extent valve 11 opens. When it is a pleural chest cavity being drained, the patient airflow is usually the result of air flowing through a hole in the patient's lung into chamber 7. Suction chamber 3 communicates with suction regulator 5 via a passage 77.

Occasionally, as when a hole in the patient's lung closes during the drainage process, chamber 7 develops a pressure even more negative than the control suction of suction chamber 3, and flap valve 11 locks shut to isolate the two chambers from each other, to therein prevent the dangerous possibility of reverse air flow into the patient. A patient negativity measuring device 23 is provided to indicate the extent of the negativity. Device 23 includes a patient negativity diaphragm 25 extending over an opening in the outer wall of chamber 7, a push rod 26 attached to diaphragm 25 and a dial 27 mounted on a pivot 29 movable by push rod 26 for cooperating with an appropriately calibrated scale 31. When the atmospheric pressure outside of chamber 7 exceeds the air pressure in chamber 7, diaphragm 25 flexes inwardly rotating dial 27 clockwise according to the amount the diaphragm flexes to therein measure and indicate the extent of patient negativity. The pivot point 29 of dial 27, or the connection point to push rod 26, can be equipped with a spring to urge the dial back to its zero position when the pressure differential gets smaller.

Suction regulator 5 for performing the functions of regulation and measurement of the suction in chamber 3 is shown in FIG. 1. Suction regular 5 includes a wall 41; a partition 43 dividing regulator 5 into an upper chamber 45 and a lower chamber 47; an opening 49 in partition 43; a light ball 53 whose diameter is slightly more than the diameter of the opening 49; a cantilever support arm 55 having a threaded bore through which extends a threaded bolt 57 with an adjustment knob 58 (which could have detents to avoid accidental changes) and disposed on a support shelf 59; a spring 61 attached at one end to ball 53 and at its other end to support arm 55 for biasing ball 53 upwardly; and a dashpot 65 composed of a piston 67 attached to ball 53 and a cylinder 69 receiving the piston in sliding engagement and mounted on a support block 71. A piston chamber (not shown) is defined between the head of piston 67 and the closed bore of cylinder 69. Atmospheric airflow at pressure $P_A$ enters chamber 45 through an entrance port 75. Lower chamber 47 communicates with suction chamber 3 through a passage 77 placing both 47 and 3 at subatmospheric pressure by virtue of the connection to a hospital suction source $P_S$ at access port 4. In normal operation, the pressure in collection chamber 7 is quite close to the value of subatmospheric pressure in suction chamber 3, differing only by the pressure drop caused by the flow of air coming from the patient. As explained above, chamber 7 will only be at a lower pressure than chamber 3 if patient negativity is greater than the suction found in chamber 3.

Figure 2:
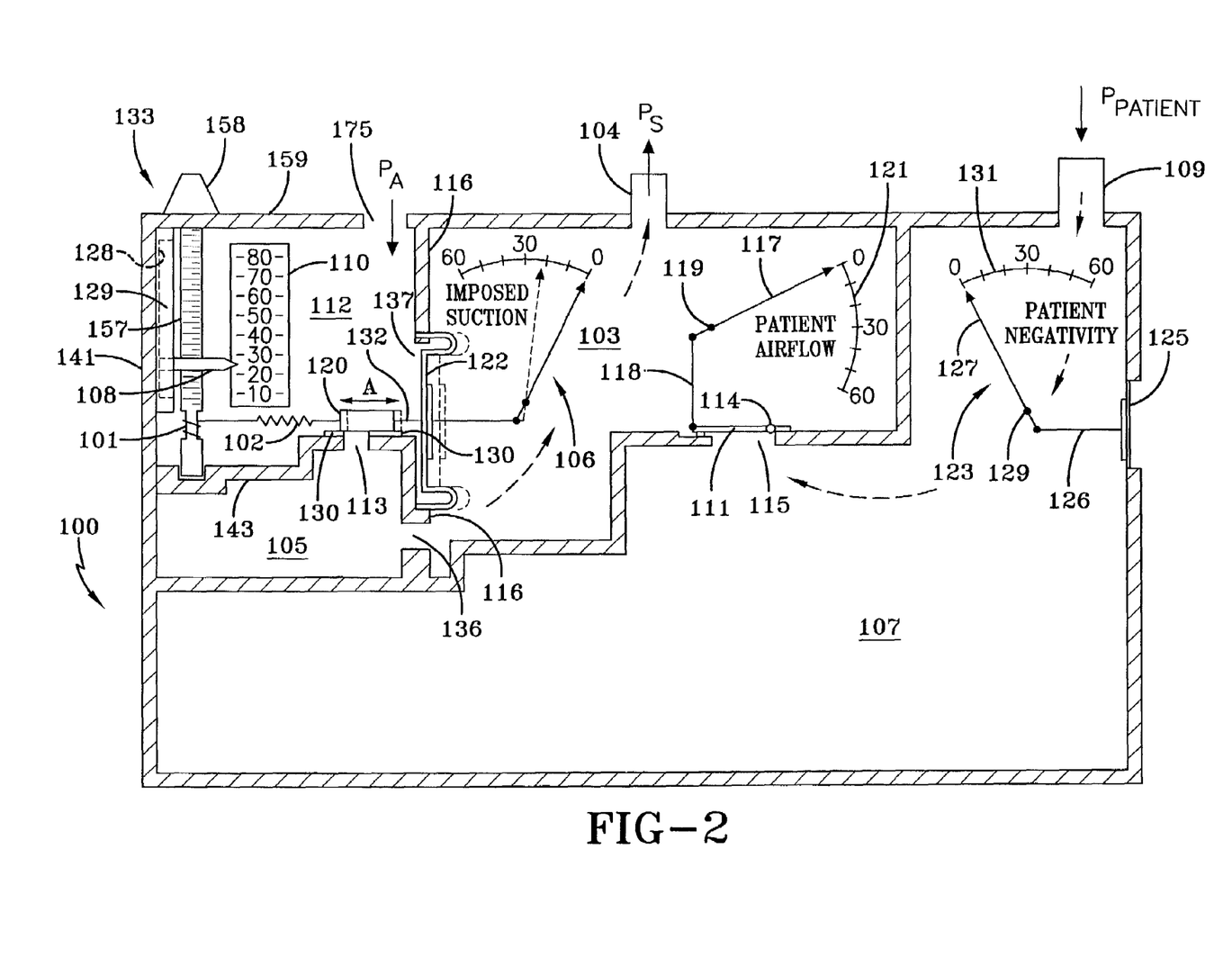
FIG. 2 is a schematic front view of the suction regulator according to a preferred embodiment of the present invention showing a convoluted diaphragm and movable door for controlling suction, a calibrated scale for setting the suction, and a second calibrated scale showing the imposed, or actual value of suction, all of which are incorporated in a fluid drainage system according to the invention.

Herein, a fluid drainage system 100 according to an embodiment of the invention is shown in FIG. 2 and represents a modified version of FIG. 1 showing the improved suction regulator controlling the input flow of atmospheric air without any type of damping device as disclosed in the prior art systems.

Referring to FIG. 2, fluid drainage system 100 includes a suction compartment or chamber 103, a suction regulator 105 and a fluid collection compartment or chamber 107. Suction regulator 105 has a port 175 open to the atmosphere at atmospheric pressure $P_A$. Suction chamber 103 has a port or opening 104 for connection to a suction source at a pressure $P_S$, a suction measuring device 106, and a patient airflow rate gauge composed of pointer 117 pivotal on a hinge 119 from a push rod 118 for movement across a calibrated scale 121. Collection chamber 107 includes a patient negativity device 123 for measuring the pressure in a patient and will only measure a value of suction or negativity greater than that found in suction chamber 103 if the hole in the patient's lung has closed. The components of fluid drainage system 100 in FIG. 2 have components identical or similar to the same numbered components in the prior art system 10 of FIG. 1, and in most cases, bearing the same numerical identifiers as those of FIG. 1 but in the 100's scale in FIG. 2.

Thus, suction chamber 103, with its suction measuring device having a dial scale and pointer 106, patient airflow flap valve 111 mounted on hinge 114 across airflow port 115 between collection chamber 107 and suction chamber 103 are all like the corresponding parts in FIG. 1. Suction port 104 is like port 4 in FIG. 1. Collection chamber 107 with patient negativity device 123 having a push rod 126 extending from a patient negativity diaphragm 125 for moving dial 127 across scale 131 are also like the corresponding parts in FIG. 1. With reference to suction regulator 105, wall 141, cantilever support arm or pointer 108 with threaded bolt 157 and adjustment knob 158 disposed on support shelf 159 are all similar to corresponding parts of FIG. 1, namely to wall 41, support arm 55 with bolt 57, and knob 58 on shelf 59 as is atmospheric air entrance port 175. However, there are significant improvements in the suction regulator 105 in the present invention as discussed below.

Suction regulator 105 has threaded bolt 157 with waist 101 as described above, which has pointer 108 operatively arranged relative to a scale 110 for indicating suction settings in terms minus centimeters of water ($-cmH_2O$). A generally horizontal wall or dividing member 143 (although it need not be horizontal as discussed below) extends across suction regulator 105 between wall 141 and a wall 116. An opening or air flow port 113, defined by surfaces having a contour (which can be flat or not flat), extends through wall 143, and a slide or thru-put door 120 connected to spring 102 moves over opening 113. A convoluted diaphragm 122 extends across an opening 137 in wall 116, and a connecting member 132 interconnects diaphragm 122 and door 120. Another opening 136 through wall 116 provides a path for any atmospheric air that comes through opening 113, and after which it flows into the suction source $P_S$ through opening 104 in suction chamber 103, all of which serve to provide the desired control of suction in chamber 103.

Scale 110 is an indicator for setting the selected value of suction in suction chamber 103, and dial scale and pointer 106 will show the actual, measured value for the imposed suction and may or may not be used in a typical chest drainage system. System 100 thus includes suction regulator 105, wall 116 separating the system into an atmospheric chamber 112 and low-pressure or suction chamber 103, and air pressure controlling apparatus, such as a convoluted diaphragm 122, and three airflow ports 175, 104 and a port 109. It is of course appreciated that convoluted diaphragm 122 can be replaced with a standard diaphragm, a bellows or any other type of comparable regulating apparatus conventional in the art that is able to move with a change in fluid pressure. Port 175 provides chamber 112 of suction regulator 105 with access to air at atmospheric pressure $P_A$ or $P_{atm}$, second port 104 provides access to a suction line (as is common in hospitals) having a pressure $P_S$ or $P_{suction}$, and third port 109 connected to fluid collection chamber 107 provides access to a patient's chest cavity $P_{patient}$ and any airflow or fluids that must be extracted by virtue of the suction pressure provided by suction chamber 103. As explained above, thru-put door 120 is connected to convoluted diaphragm 122 by means of a connecting member 132, which can be any such member that is conventional in the art, such as a very thin lightweight rod or even a section of string. Door 120 regulates the flow of atmospheric air according to its position covering opening or flow port 113.

As noted earlier, door 120 is under the bias of tension spring 102, which is connected to a regulating apparatus, such as a spring regulator 125, and which in turn is adjustable so that the tension of spring 102 can be varied. Spring regulator 133 can be a calibrated, detented dial, or smoothly varying dial setting, or adjustment knob 158 (mentioned above) for varying the tension of spring 102. Support pads 130 forming part of wall 143 provide the supporting surface for the movement of door 120. The engaging surfaces of support pads 130 and door 120 can be provided with a coating for reducing friction, such as Teflon or any other comparable friction reducing material. Ball or other bearings can support door 120 on pads 130. The variable opening of door 120 as described will control the flow of atmospheric air as needed to maintain a selected level of pressure, i.e., suction, in the control space or suction chamber 103.

The setting on spring regulator 133 is accomplished by instruction to the user in accordance with calibrated scale 110 shown on the face in FIG. 2. The tension on spring 102, and therefore the suction setting, is accomplished through connecting member 132 connected to the door on one side and on the other side, to a secure surface on the center of diaphragm 122. The other side of the door is connected to spring 102, the other side of which is connected to threaded shaft 157 which rotates with the rotation of adjustment knob 158. The value of the desired suction is indicated by the position of threaded pointer 108 as it moves up and down on threaded shaft 157. Pointer 108 in this figure, and other members connected to rotating shafts throughout, will all be held from rotation themselves by having one end ride in a slot 128 such as that provided by a guide member 129. The value of the suction pressure in chamber 103 provides one force on diaphragm 122, and the force of spring 102 puts an opposing force on diaphragm 122. The greater the force applied by spring 102 on diaphragm 122, the greater the amount of suction required to move diaphragm 122 to the right in FIG. 2, and therefore, to increase the opening of door 120. The opening and closing movement of door 120 is shown schematically by arrow A.

Figure 3:
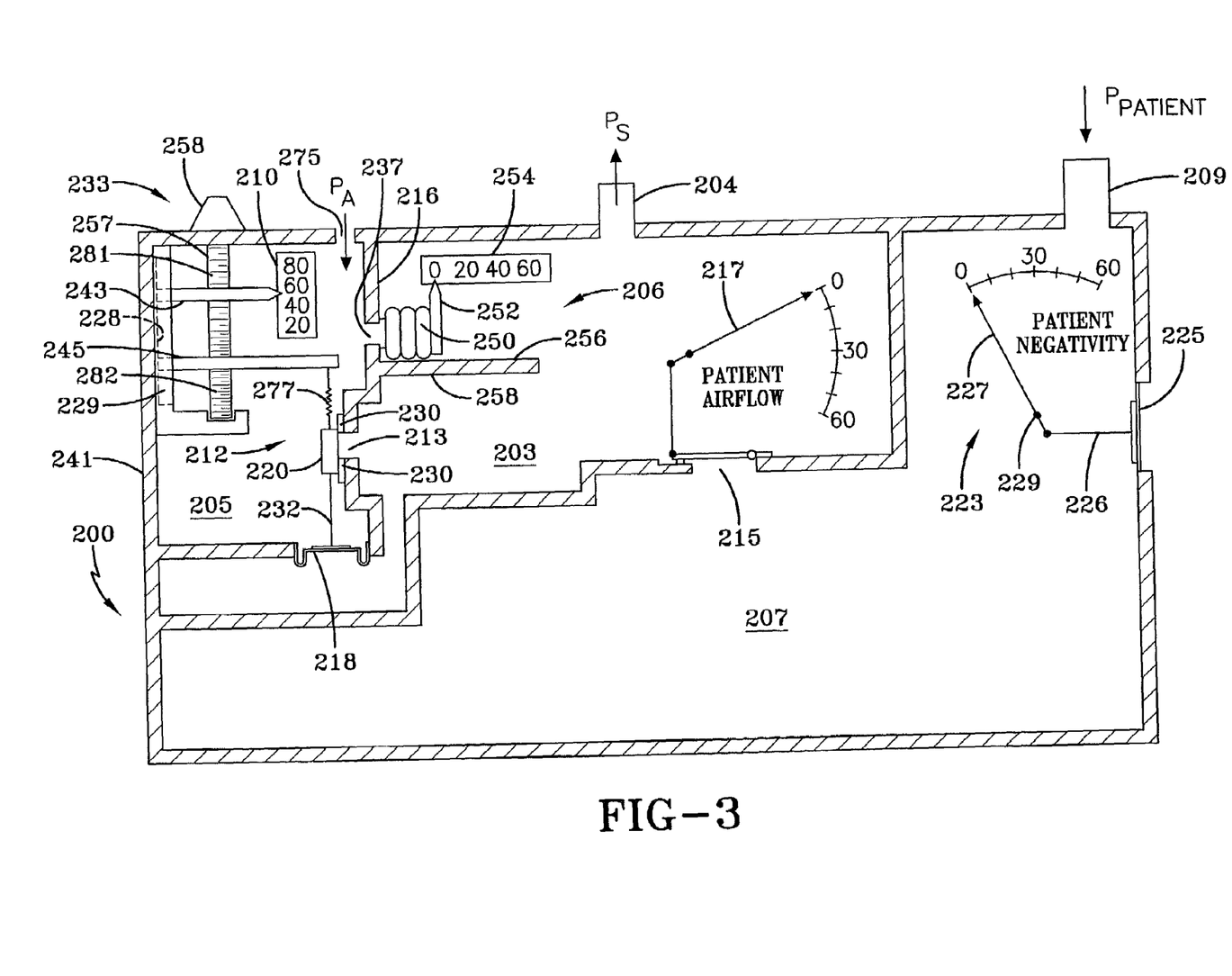
FIG. 3 illustrates an embodiment of the invention in schematic form for controlling suction with a pressure sensitive convoluted diaphragm and movable door in an axis perpendicular to that of FIG. 2 as well as a bellows activated reading of imposed suction.
Figure 4:
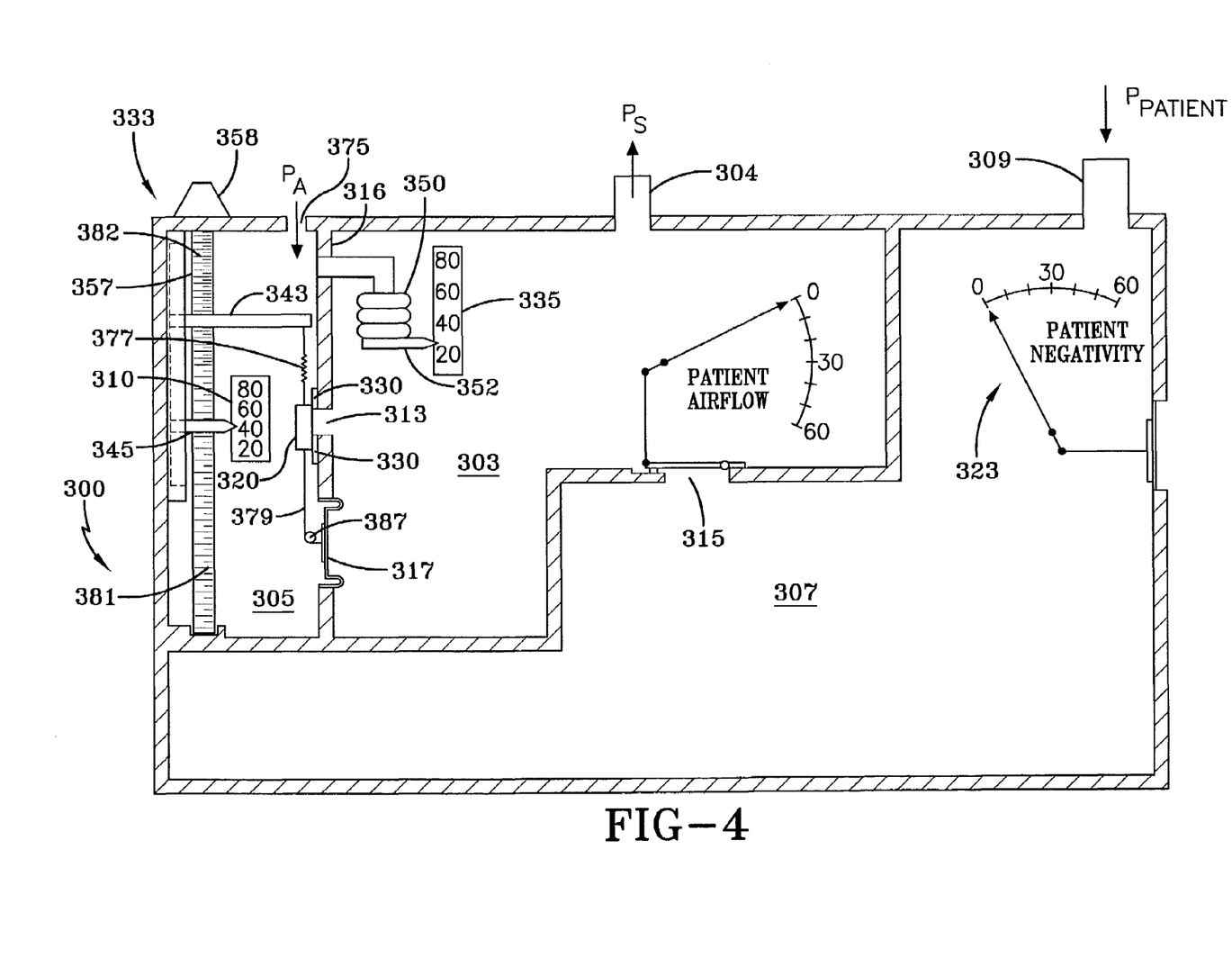
FIG. 4 illustrates an embodiment of the invention also in schematic form for controlling suction with a pressure sensitive convoluted diaphragm and movable door on the same axis as well as a bellows activated reading of imposed suction in an axis perpendicular to that of FIG. 3.

FIG. 3 is a variation of FIG. 2 with the opening and movable door 220 oriented in the vertical axis. The fluid drainage system is shown as item 200. Many components are essentially the same, and are shown with the same numerals as those in FIG. 2, but in most instances under the 200 series (member 157 of FIG. 2 becomes 257 in FIG. 3) where the components are identical or similar to those of FIG. 2. Reference can be made to the earlier discussion with respect to those components. However, two differences are noted. First, a bellows 250, with a pointer 252, will move pointer 252 across a calibrated scale 254 as an indicator of the actual suction in chamber 203, bellows 250 being connected across an opening 237 in wall 216. Bellows 250 will ride on a set of rollers or a lubricious surface 256 on a platform 258 as it moves with changes in suction. Platform 258 is needed because bellows 250 is generally pliable for easy movement, and will sag if used in the horizontal axis without support. (It should be appreciated that bellows 250 and scale 254 can easily be oriented in the vertical axis as shown in FIG. 4 as items 350 and 352, in which case a platform is not needed since the light weight needle will be located at the bottom of the hanging bellows.). The second significant difference shows shaft 257 with two movable members 243 and 245 rather than just pointer 108 as in FIG. 2. Pointer 243 is located on a part of shaft 257 with coarse threads 281 so that small amounts of rotation on shaft 257 will cause large distances of travel for pointer 243. By the same token, member 245 to which spring 277 is attached, is located on a part of shaft 257 with very fine threads 282 to therefore cause small changes in spring tension as shaft 257 is rotated. This represents a variation of the two diameters on shaft 157 as shown in FIG. 2.

FIG. 4 is a variation of FIGS. 2 and 3, and like parts are in most cases given the same numbers as those in FIG. 3 but under the 300 series. In FIG. 4, a door 320 moves across an opening 313. Door 320 and opening 313 have parallel axes, which in FIG. 4, as in FIG. 3, are vertical. While shown on the vertical axis, the same could be accomplished on any axis of choice. All components are essentially the same. However, in the case of FIG. 4, a member 379, which in the embodiment shown is flexible, connects a convoluted diaphragm 317 to door 320, and in so doing, passes over a roller 387, which translates the left right movement of diaphragm 317 to a corresponding vertical movement on door 320, therein controlling the opening and closing of thru-put path 313 between the atmosphere and suction chamber 303. As in FIG. 3, a bellows 350 will move its pointer 352 across calibrated scale 335 as an indicator of the actual suction in chamber 303; however, in this case, bellows 350 is hanging in the vertical axis thus avoiding the use of a supporting platform. Also as in FIG. 3, shaft 357 has two movable members 343, 345 rather than just one, but in this case, the coarse and fine threads 381, 382 are reversed because the functions of the respective arms 343, 345 are reversed. Having both active members 320, 317 on the same plane will serve to reduce the overall size of the unit.

Although the apparatus for moving door 120, 220, or 320 have been described as a convoluted or standard diaphragm in FIGS. 2, 3 and 4, it could also be a bellows or some other comparable device that is able to move with the change of fluid pressure, the amounts being commensurate with the pressures involved for any particular situation.

Figure 5A:
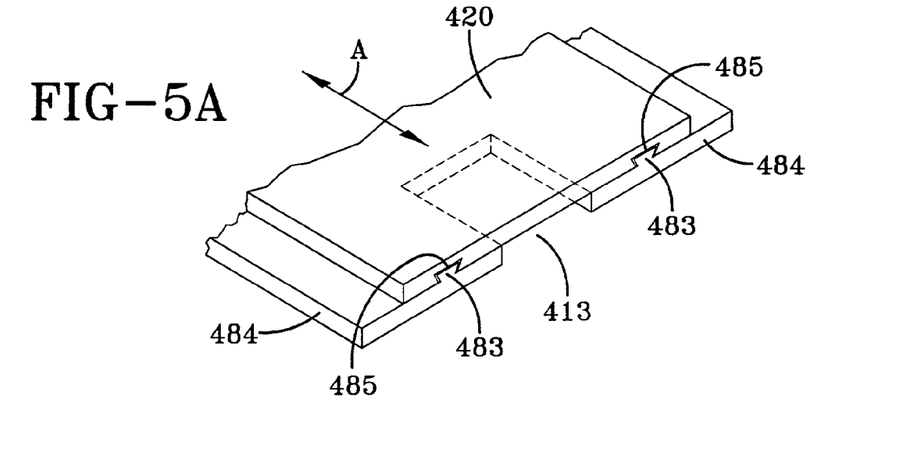

FIG. 5 illustrates several methods for capturing a movable door 420, i.e. one corresponding in purpose to doors 120, 220 or 320. FIG. 5A shows an assembly provided with guide rails 483 extending from a pair of support pieces 484 (which surfaces define the opening for path 413) to prevent the movement of door 420 away from thru-put path 413, while still being able to slide back and forth to facilitate a change in thru-put path 413 as the demand on suction changes.

Rails 483 are shown as dove tail rails, and correspondingly shaped grooves 485 in door 420 enabling the sliding motion without the separation of door 420 from support pieces 484.

Figure 5B:
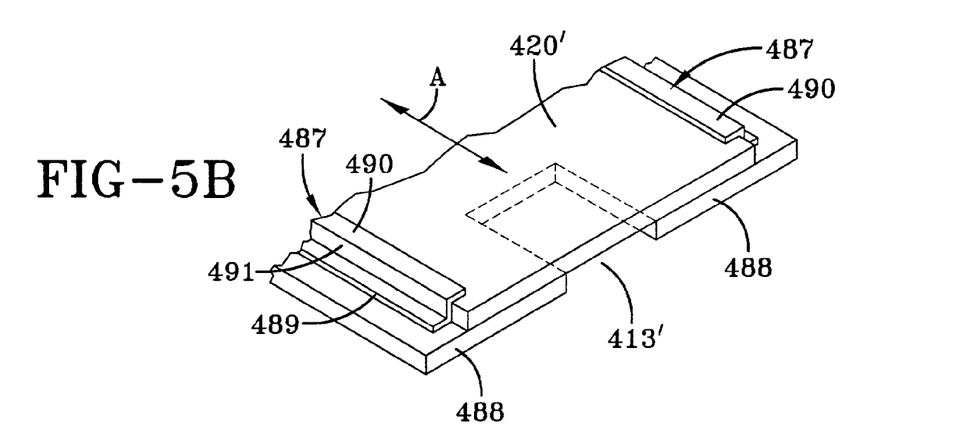

FIG. 5B provides brackets 487 extending from support pieces 488 for capturing door 420'. Brackets 487 each are attached to support piece 488 by an appropriate connector of a foot portion 489 to support piece 488, and a flange 490 extends from a leg 491 to overlap door 420'.

Figure 5C:
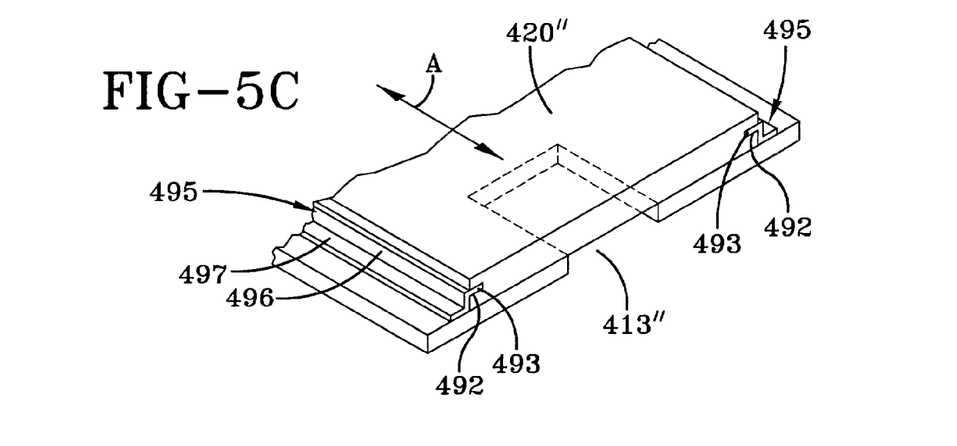

Referring to FIG. 5C, this figure, shows a door 420" with slots 492 running along each of the opposite edges of door 420", into which extend the bent-over longitudinal rims 493 of guide members 495. Members 495 have legs 496 extending from foot portions 497.

As described above, doors 420, 420' and 420" can ride on a coating of lubricious material such as Teflon. Alternatively, but not shown, the door can advantageously ride on ball bearings to further decrease the effect of frictional drag when the members are pressed together as a function of the differential pressure. A layer of felt, or the like, can be placed between the surfaces to further assist the seal so as to restrict the flow of air to the designated opening.

Figure 6:
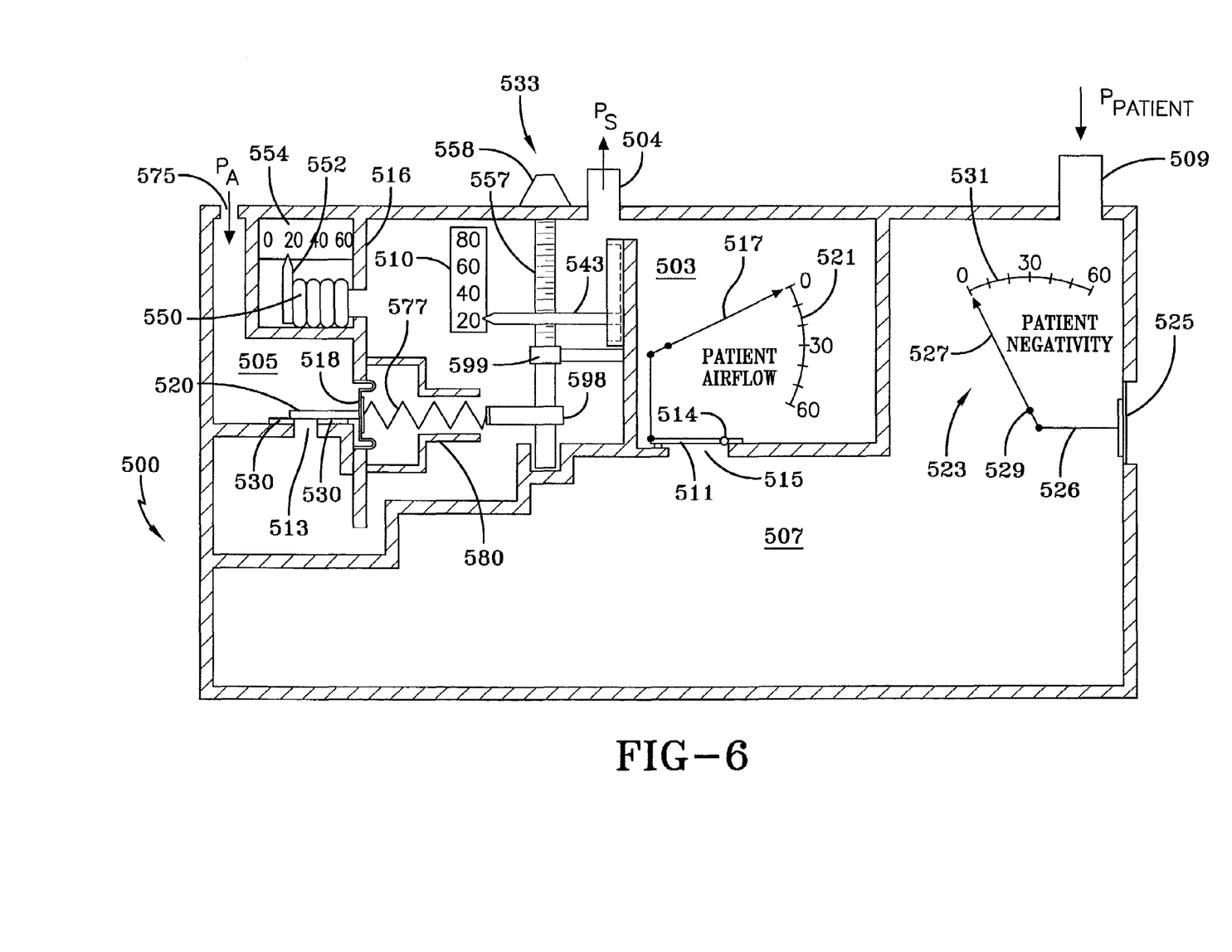
FIG. 6 is a schematic front view of an embodiment for controlling suction using a compression spring and a rotating cam for exerting the variable control force on the spring and sliding member.

A variation of FIGS. 2, 3 and 4 is shown in FIG. 6; however, it will work in the same manner. All components are also essentially the same, and those with the same general structure are shown with numerals in most cases increased by 200 from those of FIG. 4.

In FIG. 6, a suction chamber 503, suction regulator 505 and collection chamber 507 are present as in the other embodiments, connected respectfully to a suction source through port 504, the atmosphere through port 575 and the patient's chest cavity through port 509. Suction chamber 503 has a patient air-flow rate indicator having dial 517 movable across scale 521, and a one-way valve 511 pivotal on a hinge 514 for closing port 515 to collection chamber 507 when the pressure in suction chamber 503 exceeds that of collection chamber 507. A patient negativity measuring device 523 with dial 527 movable across scale 531 by means of the movement of a patient negativity diaphragm 525 extending across an opening in a wall of collection chamber 507 on the other side of which is the atmosphere. Tension springs 102, 277 and 377 of FIGS. 2–4 are replaced by a compression spring 577 in FIG. 6. A support tube 580 prevents spring 577 from sagging and spring 577 is variably compressed with a cam 598 as a shaft 557 rotates with the turning of an adjustment knob 558. As the diameter of cam 598 changes, so will the compression on spring 577. The greater the compression force of spring 577, the more suction required to enable the flexing of a convoluted diaphragm 518. Adjustment knob 558 advantageously has a sealing member to prevent atmospheric air from leaking into suction chamber 503. Sealing adjustment member 558 will serve to maintain the preferential flow feature. (Preferential flow means that the suction chamber first draws whatever air is necessary to achieve a desired suction pressure from the patient through the collection chamber, and only if that air does not provide the necessary suction pressure, is atmospheric air drawn from the suction regulator.). The preferential feature is also found in U.S. Pat. No. 4,889,531. As with FIGS. 2–4, the movement of adjustment shaft 557 must provide greater movement to pointer 543 than it does to the changes on spring 577. In this case, reduced spring movement is provided by a gear reduction coupling 599 located along shaft 557, wherein, several rotations of the adjustment rod 557 will only produce a single rotation of cam 598 as it varies system suction from its minimum to maximum values. The system of FIG. 6 will also allow for a smaller overall device because of the spring being located in the suction chamber.

Referring to the other aspects of the embodiment shown in FIG. 6, a bellows 550 moves, according to the suction imposed, through an opening in a wall 516 between suction chamber 503 and suction regulator 505 to move a pointer 552 across calibrated scale 554. Scale 554 is calibrated as minus centimeter water (–cmH$_2$O) to show the amount of imposed suction. Air enters suction regulator 505 through a port 575. A door 520 is attached to a convoluted diaphragm 518 for movement across opening 513 defined by platforms 530.

An important aspect in this type of system is that the opening member, while not mandatory, provides the most convenient structure when perpendicular to the flow of atmospheric air. However, any angle with respect to airflow will prevent the surface contact vibration which occurs with the "poppet" or "ball and socket" system for opening and closing of the thru-put path of the prior art (i.e., which are oriented in the line of fluid flow), so long as the door is free to slide along the surface containing the opening. This invention meets this objective because the force vector from atmospheric pressure and the resulting airflow will serve to force door (120, 220, 320) (FIGS. 2–4) or (520) (FIG. 6) more or less firmly against support (130, 230, 330) (FIGS. 2–4) or 530 (FIG. 6). However, since door (120, 220, 320, 520) cannot move up and down in the vertical axis as shown in greater detail in the FIG. 5 (420, 420', 420"), it will not experience surface contact vibration even though a damping device is not involved.

In operation, a patient is hooked up to air and fluid input port (109, 209, 309, 509) (FIGS. 2–4, 6). Port (104, 204, 304, 504) (FIGS. 2–4, 6) is connected to a suction line, and port (175, 275, 375, 575) (FIGS. 2–4, 6) is open to the external atmosphere. Spring (102, 277. 377, 577) (FIGS. 2–4, 6) is set by spring regulator (101, 245, 343, 598) (FIGS. 2–4,6) to establish the desired pressure differential. As the pressure across diaphragm (122, 218, 317, 518) (FIGS. 2–4, 6) varies because of pressure differential by the air in chambers (103, 203, 303, 503) (FIGS. 2–4, 6), and that of spring (102, 277, 377, 577) (FIGS. 2–4, 6), diaphragm (122, 218, 317 or 518) (FIGS. 2–4, 6) moves to a dotted line position as shown in FIG. 2 to move door (120, 220, 320, 520) (FIGS. 2–4, 6). This regulates the flow of atmospheric air from chamber (112, 205, 305, 505) (FIGS. 2–4, 6) to chamber (103, 203, 303, 503) (FIGS. 2–4, 6) and thus controls the pressure on the chest cavity and the resulting flow of air from the patient if an air leak is present. This suction pressure will also serve to drain fluids from the patient's chest cavity, or to re-inflate a collapsed lung, even in the absence of an air leak of any kind.

Figure 7:
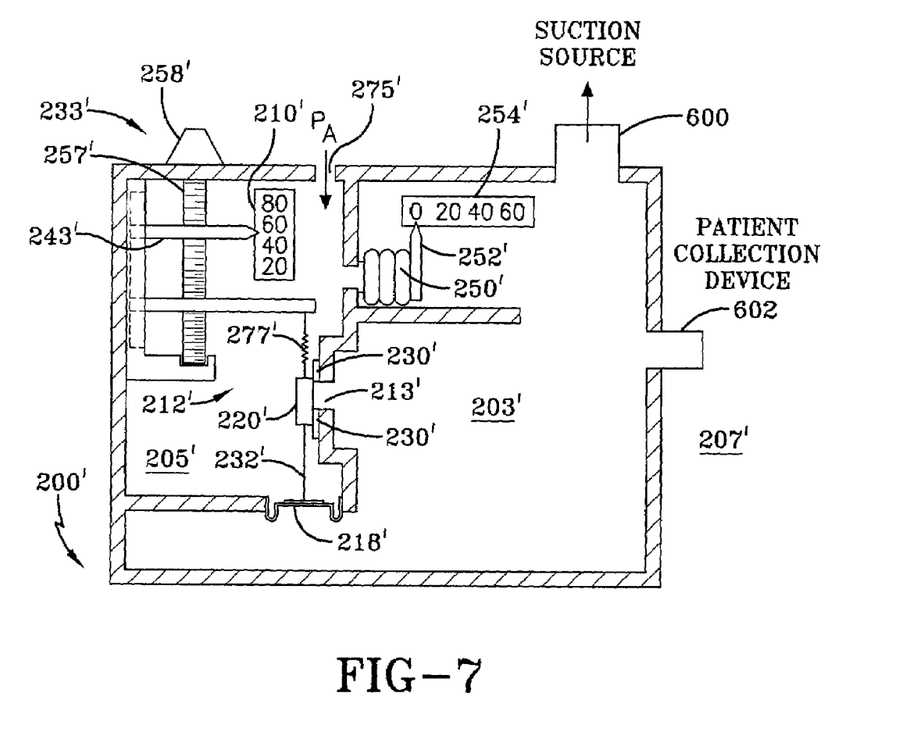
FIG. 7 is a schematic front view of a portion of FIG. 3 illustrating the suction regulator performing as a stand-alone device according to the invention.

FIG. 7 illustrates the suction regulator as a stand-alone device. While the stand-alone regulator could have been taken from any of the figures describing the suction regulator, FIG. 7 is generally the format shown in FIG. 3, and uses the same numbers therein to describe its operation, but only with a prime (') sign. The stand-alone embodiment has particular utility in hospitals with committed thoracic and/or cardiac units where virtually all patients will require a chest drainage device following their surgical procedures. In such cases, an inexpensive, permanently installed, stand-alone regulator 200' is attached to the suction source of every bed with an appropriate plumbing connection 600. The health care workers can then use a far less expensive drainage device by using port 602 to connect a unit having the collection chamber and one-way valve for patient airflow, but which does not require the function normally included for suction control. This procedure provides greater economy to the healthcare facility.

While the doors described above have been found most useful for covering the opening between the suction regulator and the suction chamber, there are many other devices available. These include a pair of movable members defining a variable opening between them, devices on the order of diaphragm leaves such as those found in certain camera systems and slidable over each other to vary the size of the opening and the like.

Finally, while all of the atmospheric air thru-put openings (113, 213, 313, 413, 513 and 213') in FIGS. 2–7 are rectangular in shape, it is appreciated that any thru-put geometry may be used, and in some cases quite advantageously. For example, circular, oval, triangular or other forms of thru-put opening are applicable, and decisions about which to use will often depend on other device parameters such as the spring constant, which is sometimes dictated by space constraints. External conditions may also play a part, one example being suction systems that are subject to wide ranges of demand on source suction. Characteristics of this type may be more effectively dealt with if the atmospheric air thru-put path is selected accordingly. Device requirements and/or conditions of use other than those mentioned, may dictate the design parameters and techniques selected.

This is an extremely simple device, and the fact that a dashpot or other damper is not required makes this an extremely efficient yet economical apparatus. It can be produced in large quantities for commercial use, yet is surprisingly inexpensive.

The invention has been described in detail with particular emphasis on the preferred embodiments, but variations and modifications within the spirit and scope of the invention may occur to those skilled in the art to which the invention pertains.

What is claimed is:

1. A system for regulating suction pressure, said system comprising:
   a suction chamber connectable to a suction source to create subatmospheric pressure within said suction chamber;
   an atmospheric chamber communicable with said subatmospheric chamber, said atmospheric chamber being exposed to the atmosphere to create atmospheric pressure within said atmospheric chamber;
   a dividing apparatus for dividing said suction chamber and said atmospheric chamber, said dividing apparatus having an opening for rendering said suction chamber and said atmospheric chamber in communication with each other;
   a movable member for varying the size of said opening between an open position and a closed position;
   a biasing device for imposing a biasing force on said movable member to bias said movable member towards the open or the closed position; and
   a pressure sensing apparatus operatively connected to said movable member for generating a force on said movable member opposite to the biasing force for effecting movement of said movable member in accordance with changes in the pressure differential between said suction chamber and said atmospheric chamber to vary the size of said opening to regulate the airflow around said movable member from said atmospheric chamber to said suction chamber to accordingly regulate the pressure in said suction chamber;
   said movable member being mounted near said opening for not vibrating in response to the airflow through said opening, and said system having no means for damping said movable member.

2. A system according to claim 1 and further including pressure regulating apparatus for setting said system to achieve a desired suction pressure in said suction chamber.

3. A system according to claim 2 wherein said biasing device is operatively connected to said pressure regulating device for establishing the biasing force on said movable member.

4. A system according to claim 3 wherein said pressure regulating device is a setting member movable to a position according to the desired suction pressure, and said biasing device is at least one spring operatively connected at one end to said setting member and to said movable member.

5. A system according to claim 4 wherein said pressure regulating device further includes an adjustment member connected to said setting member for moving said setting member to vary the biasing force.

6. A system according to claim 5 wherein said adjustment member is an adjustment knob calibrated according to specific values of suction pressure.

7. A system according to claim 4 wherein said spring is selected from the group comprising a compression spring and a tension spring.

8. A system according to claim 4 wherein said setting member is a threaded shaft, and said at least one spring is operatively connected to said shaft, the bias force of said at least one spring varying with the rotation of said shaft.

9. A system according to claim 4 wherein said setting member is a movable threaded shaft, and said system further including:
   a calibrated scale indicating specific values of suction pressure in said suction chamber;
   a pointer mounted on said shaft and movable along said scale in response to the movement of said threaded shaft to indicate a selected value of suction pressure in said suction chamber.

10. A system according to claim 9 wherein said shaft has a wider diameter for the threaded portion upon which said pointer is mounted and a narrower width, and wherein said at least one spring has an end secured to said narrower width, the value of the biasing force of said at least one spring varying in accordance with the movement of said shaft with respect to said at least one spring.

11. A system according to claim 9 wherein said shaft has a thread with a coarse pitch upon which said pointer is mounted, and a thread with a fine pitch, and wherein said pressure regulating apparatus is mounted on the width of said shaft and movable with movement of said shaft to change the biasing force on said movable member.

12. A system according to claim 9 and further including a gear reduction coupling operatively connecting said setting member to said biasing device for varying the biasing force in response to movement of said setting member by an amount reduced from the movement of said pointer along said scale.

13. A system according to claim 1 wherein said opening is defined by surfaces, and further including capturing apparatus for capturing said movable member and holding said movable member against said surfaces to prevent movement of said movable member away from said opening.

14. A system according to claim 1 wherein said pressure sensing apparatus is selected from the group consisting of a diaphragm and a bellows.

15. A system according to claim 14 wherein said diaphragm is selected from the group consisting of a standard diaphragm and a convoluted diaphragm.

16. A system according to claim 1 and further including a calibrated scale indicating values of suction pressure in said suction chamber, and further including pressure regulating apparatus for setting said system to achieve a desired suction pressure in said suction chamber and comprising an indicator for cooperating with said scale to indicate the actual value of suction pressure in said suction chamber.

17. A system according to claim 1 wherein said biasing device includes:
   a tension spring for imposing a tension biasing force on said movable member, and
   a calibrated scale operatively associated with said tension spring for measuring the tension biasing force; and
   wherein said system further includes:
      a pressure regulating apparatus for setting said system to achieve a desired suction pressure in said suction chamber, said pressure regulating apparatus comprising:
         a movable, threaded shaft movable to a position according to a desired suction pressure in said suction chamber;
         a desired suction pressure calibrated scale indicating suction pressure values for said suction chamber; and
         an indicator movable with movement of said shaft along said desired suction pressure calibrated scale to indicate the desired suction pressure; and
      an actual suction pressure calibrated scale with values indicative of the actual suction pressure in said suction chamber;
      an indicator operatively connected to said threaded shaft and to said pressure sensing apparatus, and being operatively associated with said actual suction pressure calibrated scale for indicating the actual suction pressure in said suction chamber.

18. A system according to claim 1 wherein said movable member is a sliding door, and wherein said system further includes movement facilitating structure for facilitating movement of said door.

19. A system according to claim 18 wherein said movement facilitating structure is a support pad engageable by said door.

20. A system according to claim 1 wherein said dividing apparatus includes surfaces defining said opening, and wherein said movable member comprises a door slidable on said surfaces and over said opening; and
   wherein said system further comprises friction reducing apparatus for reducing the friction between said door and said surfaces.

21. A system according to claim 20 wherein said friction reducing apparatus is selected from the group consisting of channel guides for holding said door against said surfaces with bearings on said door for engaging said surfaces, and a friction reducing substance.

22. A system according to claim 21 wherein said friction reducing substance is Teflon.

23. A system according to claim 1 wherein said opening in said dividing apparatus is an airflow port.

24. A system according to claim 1 and further for draining fluid from a portion of a body, and further comprising:
   a collection apparatus for receiving fluids from the body, said collection apparatus including an inlet port for admitting fluids from the body, and said collection apparatus being communicable with said suction chamber.

25. A system according to claim 1 wherein said opening in said dividing apparatus lies in a vertical plane to enable a reduction in the size of said system.

26. A suction regulator for controlling the pressure in a suction chamber used in apparatus for withdrawing fluid from a patient, said suction regulator comprising:
   an opening to said suction chamber defined by surfaces having a predetermined contour around said opening;
   a closure movable across said opening to control the size of the opening and the amount of airflow between said suction regulator and the suction chamber, said closure not being subject to surface contact vibrations from the flow of air past said closure, and said suction regulator excluding means for damping any vibration in said closure;
   a bias device for exerting a bias force on said closure to bias said closure towards a position for opening or closing said opening;
   a pressure sensor for sensing the pressure differential between said suction regulator and the suction chamber; and
   a connector interconnecting said pressure sensor and said closure for exerting a pressure differential force on said closure in opposition to the bias force to control the position of said closure across said opening to establish the proper airflow through said opening.

27. A suction regulator according to claim 26 wherein the fluid is drawn from the chest cavity of a patient.

28. A suction regulator according to claim 26 wherein the bias device is adjustable to establish said bias force.

29. A suction regulator according to claim 26 wherein said closure is a door slidable across said opening in contact with said surfaces defining said opening, said bias device being connected to a supporting member and to said door for exerting the bias force on said door, and said connecting member connecting said pressure sensor to said door.

30. A suction regulator according to claim 29 and further including guiding structure for guiding said door across said opening in contact with said surfaces defining said opening.

31. A suction regulator according to claim 26 wherein said opening is in a vertical plane.

32. Apparatus for regulating the pressure at which air is withdrawn from a patient, said apparatus comprising:
   a collection chamber for receiving air subjected to pressure from a patient's chest cavity;
   a suction regulator open to the atmosphere; and
   a suction chamber subject to a suction source;
   said suction regulator having an opening to said suction chamber, said opening being defined by surfaces having a predetermined contour; and a closure device being movable across said contour for automatically controlling the size of said opening to control the amount of atmospheric pressure applied to said suction chamber in response to a predetermined change in the pressure differential across said opening, said closure not being subject to vibration from the flow of air through said opening, said apparatus excluding means for damping any vibration of said closure.

33. Apparatus for regulating the pressure at which air is withdrawn from a patient, said apparatus comprising:
   a collection chamber for receiving air subjected to pressure from a patient's chest cavity;
   a suction regulator open to the atmosphere; and
   a suction chamber separate from said collection chamber and being subject to a suction source;
   said suction regulator having an opening to said suction chamber, said opening being defined by surfaces having a predetermined contour; and a closure device being movable across said contour for controlling the size of said opening to control the amount of atmospheric pressure applied to said suction chamber, said closure not being subject to vibration from the flow of air through said opening, said apparatus excluding means for damping any vibration of said closure.

34. Apparatus for regulating the pressure at which air is withdrawn from a patient according to claim 33, wherein said suction chamber is separated from said collection chamber by a wall, said wall having a closeable opening with a valve structure for closing said opening in response to the pressure in said suction chamber exceeding the pressure in said collection chamber.

35. Apparatus for regulating the pressure at which air is withdrawn from a patient, said apparatus comprising:
   a collection chamber for receiving air subjected to pressure from a patient's chest cavity;
   a suction regulator open to the atmosphere;
   a suction chamber subject to a suction source; and
   an openable structure separating said suction chamber from said collection chamber;
   said suction regulator having an opening to said suction chamber, said opening being defined by surfaces having a predetermined contour; and a closure device being movable across said contour for controlling the size of said opening to control the amount of atmospheric pressure applied to said suction chamber in response to a difference in pressure between said collection chamber and said suction chamber, said closure device not being subject to vibration from the flow of air through said opening, said apparatus excluding means for damping any vibration of said closure.

* * * * *